US012758359B2

(12) United States Patent
Chen

(10) Patent No.: US 12,758,359 B2
(45) Date of Patent: Oct. 13, 2026

(54) ANALGESIC PROCEDURE

(71) Applicant: William H Chen Living Trust, Chesterfield, MO (US)

(72) Inventor: William H. Chen, Chesterfield, MO (US)

( * ) Notice: Subject to any disclaimer, the term of this patent is extended or adjusted under 35 U.S.C. 154(b) by 0 days.

(21) Appl. No.: 19/344,351

(22) Filed: Sep. 29, 2025

(65) Prior Publication Data

US 2026/0026914 A1 Jan. 29, 2026

Related U.S. Application Data

(62) Division of application No. 18/079,664, filed on Dec. 12, 2022, now abandoned, which is a division of
(Continued)

(51) Int. Cl.

| | |
|---|---|
| ***A61C 1/00*** | (2006.01) |
| ***A61B 18/20*** | (2006.01) |
| ***A61B 18/22*** | (2006.01) |
| ***A61C 5/50*** | (2017.01) |
| ***A61C 17/02*** | (2006.01) |
| ***A61C 17/028*** | (2006.01) |

(Continued)

(52) U.S. Cl.
CPC ............ *A61C 1/0046* (2013.01); *A61B 18/20* (2013.01); *A61B 18/22* (2013.01); *A61C 5/50* (2017.02); *A61C 17/0217* (2013.01); *A61C 17/028* (2013.01); *A61N 5/0613* (2013.01); *A61N 5/067* (2021.08); *A61B 2018/202* (2013.01); *A61B 2018/2253* (2017.05); *A61N 2005/007* (2013.01); *A61N 2005/0606* (2013.01); *A61N 2005/0659* (2013.01)

(58) Field of Classification Search
CPC ..... A61C 1/0046; A61C 5/50; A61C 17/0217; A61C 17/022; A61C 17/024; A61C 17/028; A61C 17/032; A61N 5/067; A61N 5/0613; A61N 2005/007; A61N 5/045; A61N 2005/0606; A61N 2005/0659; A61B 18/20; A61B 18/22; A61B 2018/2253; A61B 2018/202
USPC ............................................................ 433/29
See application file for complete search history.

(56) References Cited

U.S. PATENT DOCUMENTS

| | | | | |
|---|---|---|---|---|
| 2006/0240381 A1* | 10/2006 | Rizoiu | ................. | A61C 17/024 433/80 |
| 2011/0082526 A1* | 4/2011 | Rizoiu | ..................... | A61N 5/00 607/89 |
| 2019/0090998 A1* | 3/2019 | Ertl | ........................ | A61B 90/70 |

* cited by examiner

*Primary Examiner* — Aaron F Roane
(74) *Attorney, Agent, or Firm* — Fast Forward Law, LLC; David E. Crawford; Brian P. Klein

(57) ABSTRACT

A dental procedure performed on target tissue without anesthetic or anesthesia including preconditioning the target tissue using a laser device constructed to produce light in a wavelength range of 2750 nm to 11500 nm, to provide an energy fluence in a range of 50 J/cm$^2$ to 100 J/cm$^2$, and to operate in a free running pulsed mode providing 60 μm bursts at a frequency of at least 50 Hz. Preconditioning includes selecting a combination of average optical output power and preconditioning time to administer low level laser therapy. The laser device is adjusted to deliver light through the light guide of the laser device at the selected average optical output power. Light delivered through the light guide of the adjusted laser device is directed toward the target tissue for the selected preconditioning time providing analgesia to the target tissue. Oral tissue is removed from the preconditioned target tissue during analgesia.

12 Claims, 3 Drawing Sheets

Related U.S. Application Data application No. 17/750,068, filed on May 20, 2022, now Pat. No. 11,963,831.

(51) Int. Cl.

| | |
|---|---|
| ***A61N 5/06*** | (2006.01) |
| ***A61N 5/067*** | (2006.01) |
| *A61N 5/00* | (2006.01) |

ANALGESIC PROCEDURE

CROSS-REFERENCE TO RELATED APPLICATIONS

The present application is a divisional of co-pending U.S. patent application Ser. No. 18/079,664, filed Dec. 12, 2022, which is a divisional of co-pending U.S. patent application Ser. No. 17/750,068, filed on May 20, 2022, which issued as U.S. Pat. No. 11,963,831, on Apr. 23, 2024, all of which are hereby incorporated by reference in their respective entireties.

BACKGROUND

The present invention generally relates to a device and procedure for providing analgesia and more particularly, to a laser device and procedure for desensitizing a portion of a client's mouth prior to removing oral tissue.

Conventionally, dentists administer a local anesthetic before a dental procedure using a needle in a syringe to give a local infiltration or a block. Alternatively, dentists administer nitrous oxide and oxygen by inhalation to provide some analgesia and minimal sedation or give clients sedatives orally or intravenously. Each of these methods is known to effectively produce anesthesia or analgesia in clients before their dental procedures. On occasion these methods have caused side effects and complications that vary in degree from client to client. In addition, using a needle in a syringe causes many clients stress and fear, resulting in dental visits being stressful for those clients.

Some dentists avoid using needles in syringe by producing analgesia using a dental laser. For example, the laser device may include a Nd:YAG (neodymium-doped yttrium aluminum garnet) laser {1064 nm wavelength, near infrared). The laser energy passes through the enamel and dentin of a tooth to produce an analgesic effect on nerves extending through the pulp cavity of the tooth. In another example, the laser device may include an Er:YAG (erbium-doped YAG) laser (2940 nm wavelength, mid infrared) which can be used to produce an analgesic effect and to improve tissue healing using Low Level Laser Therapy. Unlike local anesthesia, laser analgesia does not produce profound numbness. Further, laser analgesia eliminates the use of a needle in a client's mouth which can greatly reduce or eliminate their stress and fear.

Some dentists have used dental lasers to remove hard tissue. Sometimes these dentists first use the laser in free running pulsed mode set to a frequency of 15 Hz to induce analgesia before removing the tissue with the laser. These dentists avoid higher frequencies when inducing analgesia because the higher frequencies are believed to increase tissue heating and pain.

In view of many persons avoiding regular dental exams and dental care due to their fear and the consequences of avoidance, there remains a need for a method of providing analgesia in target tissue in a client's mouth to perform selected dental procedures.

SUMMARY

In one aspect, the present disclosure includes a dental procedure performed on target tissue in a client's mouth without anesthetic or anesthesia. The procedure comprises preconditioning the target tissue in the client's mouth using a laser device to produce analgesia in the target tissue. The laser device has a light guide adapted to deliver light to the target tissue. The laser device is constructed to produce light having a center wavelength in a wavelength range of 2750 nm to 11500 nm, to provide an energy fluence in an energy fluence range of 50 J/cm$^2$ to 100 J/cm$^2$ and to operate in a free running pulsed mode providing 60 μm bursts at a frequency of at least 50 Hz. The step of preconditioning includes selecting a combination of average optical output power and preconditioning time to administer low level laser therapy to the target tissue in the client's mouth using the laser device. The laser device is adjusted to deliver light through the light guide of the laser device at the selected average optical output power. Light delivered through the light guide of the adjusted laser device is directed toward the target tissue in the client's mouth for the selected preconditioning time providing analgesia to the target tissue in the client's mouth. Oral tissue is removed from the preconditioned target tissue in the client's mouth during analgesia.

In another aspect, the present disclosure includes a dental procedure performed on target tissue in a client's mouth without anesthetic or anesthesia. The procedure comprises preconditioning the target tissue in the client's mouth using a laser device constructed to produce light having a center wavelength in a wavelength range of 750 nm to 1400 nm and a handpiece having an operational end from which light produced by the laser device is emitted.

Preconditioning includes adjusting the laser device to emit light having an average optical output power in a power range of 1.0 W to 2.5 W in a continuous wave mode. A predetermined target distance is maintained between the operational end of the handpiece and the target tissue in the client's mouth. While maintaining the predetermined target distance, light emitted from the operational end of the handpiece is directed toward the target tissue in the client's mouth for a time period selected to provide analgesia to the target tissue in the client's mouth. Oral tissue is removed from the preconditioned target tissue in the client's mouth during the analgesia.

Further, the present disclosure includes a dental procedure for desensitizing target tissue in a client's mouth comprising an abfraction or a cervical lesion of a tooth without using anesthetic, anesthesia, or a chemical desensitizing agent. The procedure comprises selecting a laser device including at least one laser selected from a group of lasers consisting of an Er:YAG solid-state laser, an Er,Cr:YSGG solid-state laser, and a CO2 gas laser and a handpiece including a fiber tip from which light produced by the laser is emitted. The fiber tip has a diameter in a range of 500 μm to 800 μm. The handpiece has a nozzle from which a spray comprising water and air is dispensed for cooling the target tissue in the client's mouth while light emitted by the fiber tip of the handpiece is directed toward the target tissue in the client's mouth. The laser device includes a flow control for varying a rate at which water is dispensed from the nozzle and a rate at which air is dispensed from the nozzle. The procedure includes adjusting the flow control to dispense a spray comprising water at an initial water flow rate and air at an initial air flow rate. While the flow control is adjusted to dispense the spray comprising water at the initial water flow rate and air at the initial air flow rate initial rate, light emitted from the fiber tip of the handpiece is directed toward the target tissue in the client's mouth for a first period. After the first period, the flow control is adjusted to decrease the water flow rate and the air flow rate while continuing to direct light emitted from the fiber tip of the handpiece toward the target tissue in the client's mouth for a second period.

The disclosure also includes a laser device for performing a procedure on tissue in a living animal to reduce pain perceived by the animal without anesthetic or anesthesia. The device comprises a housing and a laser unit mounted in the housing. The laser unit is configured to produce light having a center wavelength in a wavelength range of 750 nm to 1400 nm. The device also includes a handpiece operatively connected to the laser unit for administering a low level laser therapy dose having the energy fluence. The handpiece includes an operational end through which light produced by the laser unit is emitted when administering the low level laser therapy dose to the tissue. The handpiece is configured to maintain a target distance between the operational end and the tissue that is selected to ensure light emitted through the operational end is projected onto an area on the animal of one square centimeter when administering the low level laser therapy dose to the tissue.

Moreover, the present disclosure includes an ablation procedure performed on soft tissue in a client's mouth without anesthetic or anesthesia using a laser device constructed to produce light having a center wavelength in a wavelength range of 2750 nm to 11500 nm. The laser device includes a handpiece having a fiber tip though which light is transmitted. The fiber tip has a diameter in a size range of 400 μm to 1200 μm. The handpiece has a nozzle from which a spray comprising water and air is dispensed to cool the soft tissue in the client's mouth while light emitted from the fiber tip of the handpiece is directed toward the soft tissue in the client's mouth. The laser device includes a flow control for varying a rate at which the spray is dispensed from the nozzle. The procedure comprises adjusting the laser device to operate in a free running pulsed mode providing 60 μm bursts at a frequency of at least 50 Hz, and to produce light having an average optical output power in a power range of 1.75 W to 2.25 W. The flow control is adjusted to dispense water from the nozzle at a water flow rate in a water flow rate range of 10% to 20% and to dispense air from the nozzle at an initial air flow rate of 20%.

Other aspects of the present disclosure will be apparent in view of the following description and claims.

BRIEF DESCRIPTION OF THE DRAWINGS

Corresponding reference characters indicate corresponding parts throughout the drawings.

DETAILED DESCRIPTION OF THE DRAWINGS

Figure 1:
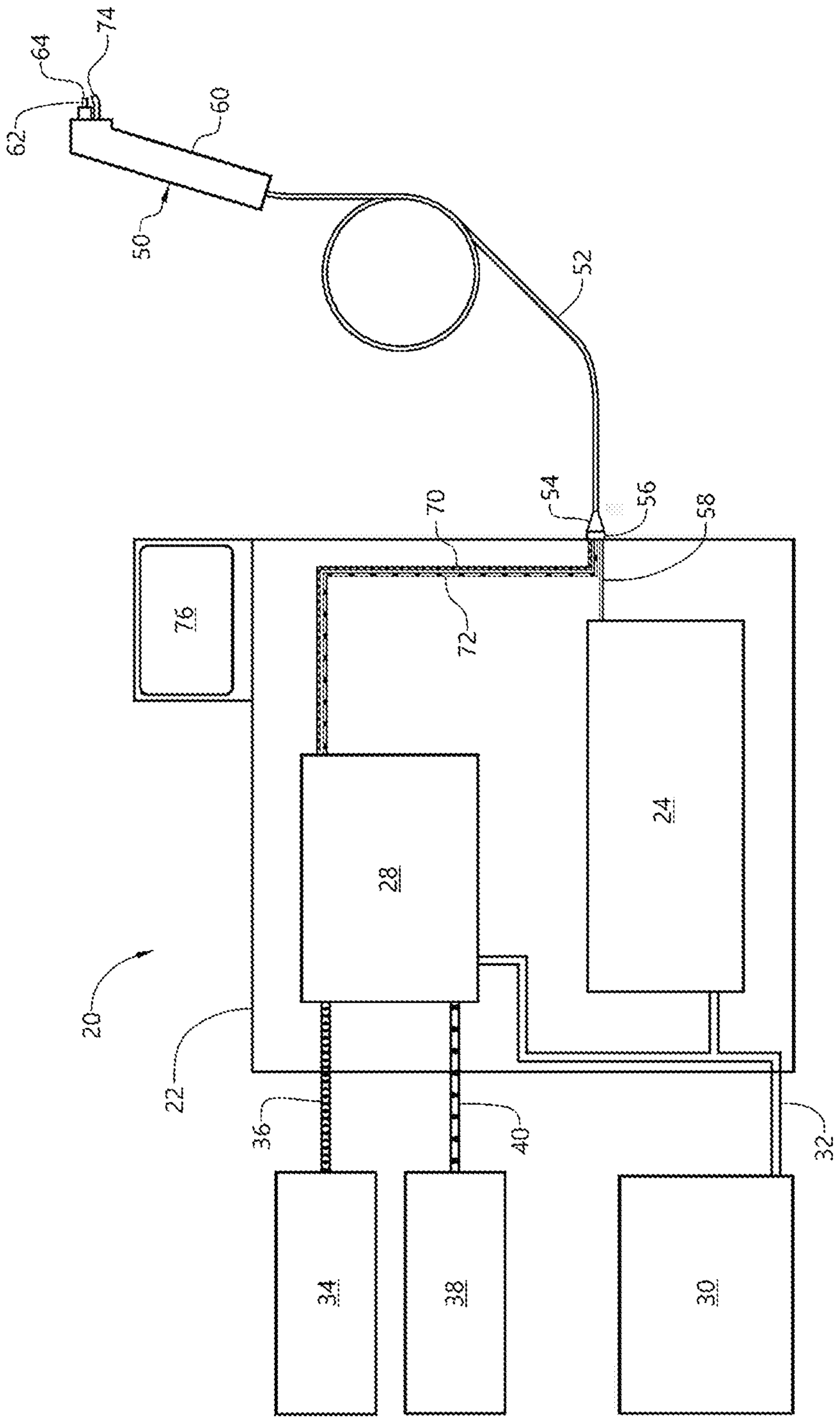
FIG. 1 is a schematic elevation of a first example of a laser device.

Referring to FIG. 1, a first example of a laser device for performing dental procedures is generally designated in its entirety by the reference number 20. As will be explained in further detail, one dental procedure for which a dentist uses this laser device 20 is to perform a preconditioning procedure on a portion of a client's mouth (e.g., a tooth) to produce analgesia without anesthetic or anesthesia. As will be appreciated, the preconditioning procedure has many potential uses in dentistry, including desensitizing a tooth before removing hard tissues such as enamel, dentin, and dental caries and soft tissues such as gingiva, labial frenula, hyperplastic gingiva, and pulp tissues.

The laser device 20 includes a housing 22 in which a laser unit 24 is mounted. In some examples, the laser unit 24 is configured to produce electromagnetic energy (e.g., light) having an energy fluence in a preselected energy fluence range and operates in a free running pulsed mode. More particularly, in some examples the laser unit 24 produces light having an energy fluence in an energy fluence range of 50 J/cm$^2$ to 100 J/cm$^2$ and operates in a free running pulsed mode at a frequency of at least 50 Hz. In some examples, the laser unit 24 operates in a free running pulsed mode at a frequency of at least 75 Hz. Although other types of lasers may be used, the illustrated unit 24 comprises a laser configured to produce electromagnetic energy having a centerline wavelength in a preselected wavelength range of 2750 nm to 11500 nm. In some examples, the laser may include an Er:YAG solid-state laser, an Er,Cr:YSGG solid-state laser, or a $CO_2$ gas laser.

When light produced by the laser unit 24 is directed toward tissue, the light energy increases tissue temperature. Conventionally, a spray consisting of air and water is used to cool the affected tissue to prevent side effects such as the tissue from being damaged by excessive heat. Accordingly, a flow control unit 28 is also mounted in the illustrated housing 22 to independently control flow rates of water and air used to cool tissue as will be explained. A remote power source 30 is operatively connected to the laser unit 24 and the flow control unit 28 by conventional electric cables 32 to provide electrical power to each unit. Further, a remote water source 34 (e.g., a tank containing distilled water) is operatively connected to the flow control unit 28 via tubing 36 to provide water to the unit and a pressurized remote air source 38 (e.g., pressurized air from a dental compressor) is operatively connected to the flow control unit via tubing 40 to supply air to the unit. The flow control unit 28 regulates flow rates of water and air.

As further illustrated in FIG. 1, the laser device 20 includes a handpiece, generally designated by 50. The handpiece 50 is connected to a conventional elongated flexible conduit or trunk 52 containing a fiber optic light guide, a water passageway, and an air passageway. A connector 54 provided on an end of the trunk 52 opposite the handpiece 50 selectively couples the trunk and handpiece to a corresponding port 56 on the housing 22 so the fiber optic light guide in the trunk aligns with a light guide 58 extending through the housing from the port to the laser unit 24. Thus, electromagnetic energy produced by the laser unit 24 is transmittable through the light guide 58 in the housing 22 and fiber optic light guide in the trunk 52 to the handpiece 50. As will be appreciated, the handpiece 50 has a grip 60 and a fitting 62 extending from the handpiece generally opposite the trunk 52 to a fiber tip 64 through which light is selectively emitted. The grip 60 is sized and shaped for being grasped by the dentist allowing the dentist to manually manipulate the handpiece 50 to direct light emitted from the fiber tip 64 toward a selected portion of the client's mouth as will be explained. When the connector 54 is coupled to the port 56, the water passageway and the air passageway in the trunk 52 are in independent fluid communication with a water tube 70 and an air tube 72, respectively, extending from the port to the flow control unit 28 to transport water and air, respectively, through the water and air tubes and the water and air passageways in the trunk to the handpiece 50. The handpiece 50 has a nozzle 74 adjacent the fitting 62 that selectively directs a spray of water and air transported to the handpiece toward the selected portion of the client's mouth to cool tissue when desired. In some examples, the nozzle 74 may include a plurality of orifices. It is envisioned that in some alternative examples, a plurality of connectors and corresponding ports may be used to independently connect the light guide 60, the water tube 70, and the air tube 72 in the housing 22 to the fiber optic light guide, the water passageway, and the air passageway in the trunk 52. Further, it is envisioned that one or both of the water and air tubes and the corresponding water and air passageways may be omitted in some examples. As also shown in FIG. 1, the laser device 20 includes a control panel, generally designated by 76, allowing the dentist to control settings such as laser power, frequency, operating modes as well as flow control settings such as flow rates of water and air delivered through the nozzle 74.

Figure 2:
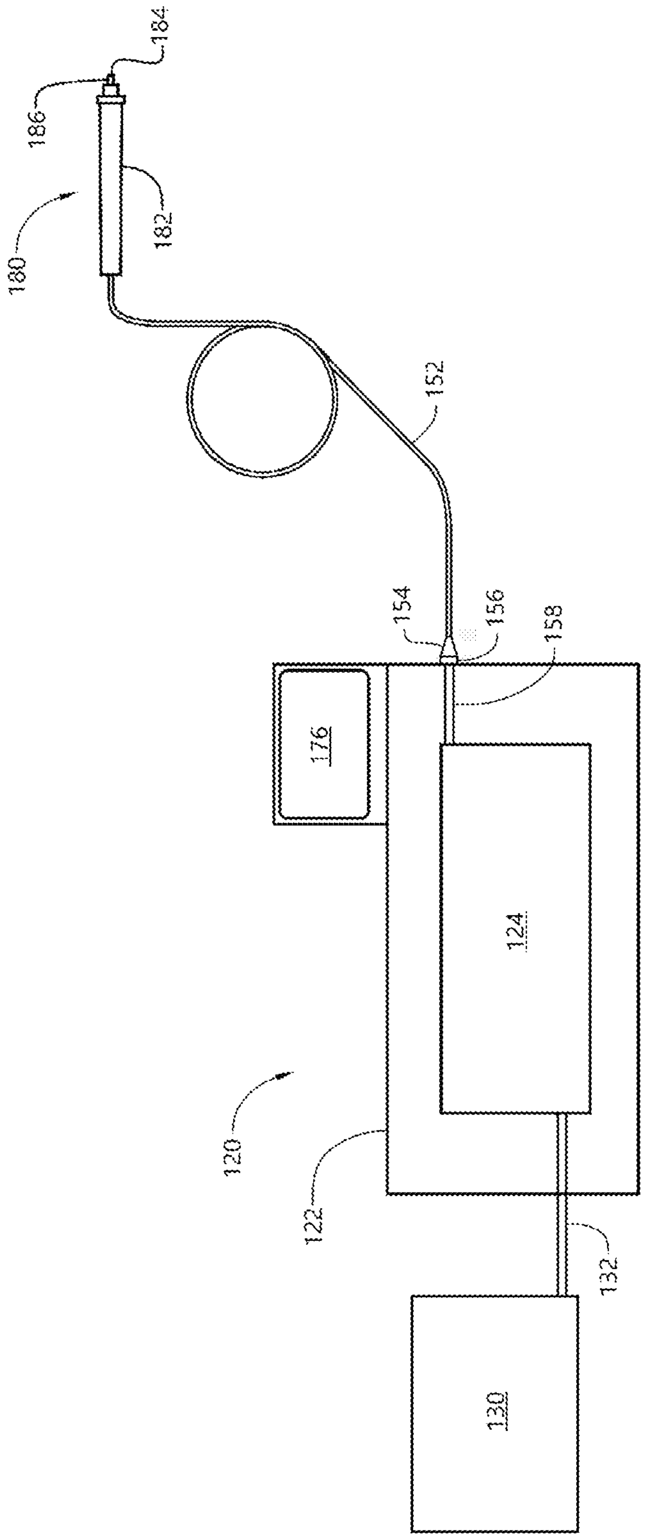
FIG. 2 is a schematic elevation of a second example of a laser device.

Referring to FIG. 2, a second example of a laser device for performing a dental procedure is generally designated in its entirety by the reference number 120. A dentist uses this laser device 120 to perform a preconditioning procedure on soft tissue in a portion of a client's mouth. The laser device 120 includes a housing 122 in which a laser unit 124 is mounted. The laser unit 124 comprises a diode laser constructed to produce light having a center wavelength of 800 nm, 810 nm, 815 nm, 940 nm, 980 nm, or 1040 nm. Further, the diode laser emits light in a continuous wave.

As further illustrated in FIG. 2, the laser device 120 includes a handpiece, generally designated by 180. The handpiece 180 is connected to a conventional elongated flexible trunk 152 containing a fiber optic light guide. A connector 154 is provided on an end of the trunk 152 opposite the handpiece 180 to selectively couple the trunk and handpiece to a corresponding port 156 on the housing 122 so the fiber optic light guide in the trunk aligns with a light guide 158 extending through the housing from the port to the laser unit 24. Thus, electromagnetic energy produced by the laser unit 124 is transmittable through the light guide 158 in the housing 122 and fiber optic light guide in the trunk 152 to the handpiece 180. As will be appreciated, the handpiece 180 has a grip 182 and an operational end 184 extending from the handpiece generally opposite the trunk 152 through which light is selectively emitted. The grip 182 is sized and shaped for being grasped by the dentist allowing the dentist to manually manipulate the handpiece 180 to direct light emitted from the operational end 184 toward a selected portion of the client's mouth. The laser device 120 also includes a control panel, generally designated by 176, allowing the dentist to adjust laser settings.

Figure 3A:
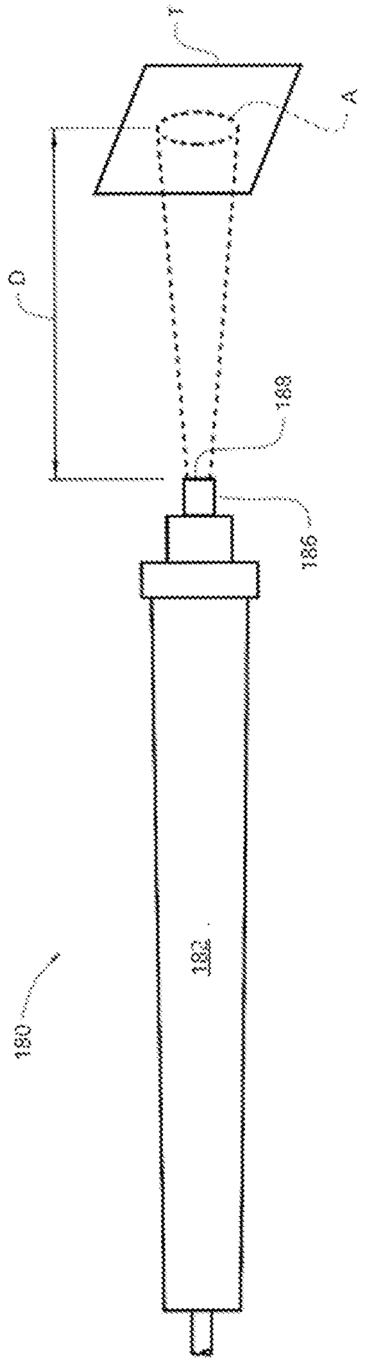
FIG. 3A is an enlarged schematic side elevation of a handpiece of the laser device of FIG. 2.

It is envisioned that the handpiece 180 may have other configurations. As illustrated in FIG. 3A, light emitted from the operational end 184 is projected onto an area A of tissue Tin the client's mouth. Light emitted from the operational end 184 diverges or spreads out, resulting in the size of the area A on which the light is projected increasing as a distance D between the operational end 184 and the tissue T increases. Further, the intensity or irradiance of light projected on the tissue T varies depending on the distance D. Shorter distances produce higher intensities. As will be appreciated by those skilled in the art, controlling the area A to be one square centimeter provides a constant unit area that simplifies area dependent variable calculations, making it convenient to calculate power, total energy, and treatment time to reach a fluence of 50 J/cm$^2$ to 100 J/cm$^2$ needed to attain the analgesia effect.

Figure 3B:
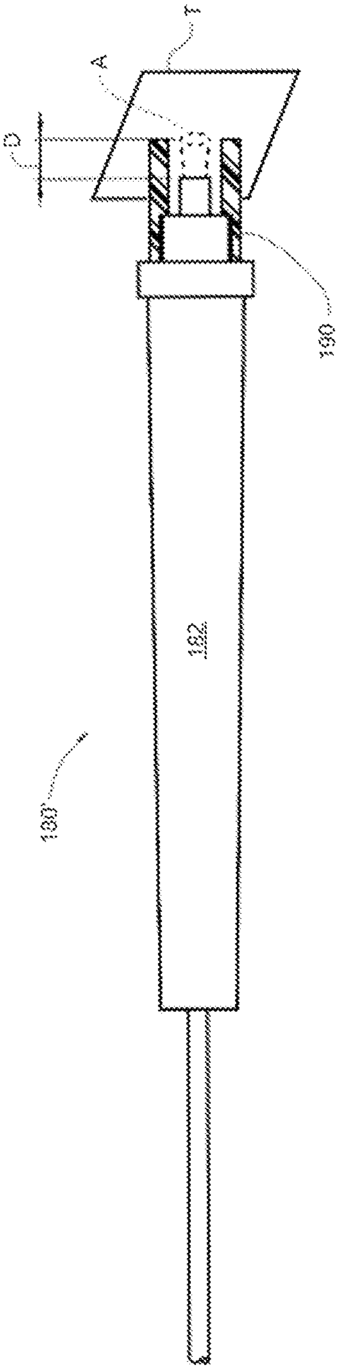
FIG. 3B is an enlarged schematic side elevation of the handpiece of FIG. 3A having a distance guide installed thereon.

As shown in FIG. 3B, an alternative handpiece, generally designated by 180', is similar to the handpiece 80 illustrated in FIG. 3A except that a guide, generally designated by 190, is selectively or permanently mounted on the handpiece. As will be appreciated, the distance guide 190 physically establishes the distance D between the operational end 184 of the handpiece 180' to a target operating distance Dm Although the target operating distance Dm may have other lengths, in the illustrated example the target operating distance is selected so the area A of light projected on the tissue T has a known target size $A_m$. For example, the target operating distance Dm may be selected so the target area $A_m$ is one cm$^2$ which simplifies energy calculations. Further, the intensity or irradiance of light projected on the tissue Tis controlled by controlling the distance D. And, because the total energy introduced to the area A is proportional to duration of exposure, the total energy introduced to the area A can be limited by limiting exposure duration. In some examples, the distance guide 190 is transparent to permit the dentist to confirm tissue is being exposed to the light.

As those skilled in the art will understand how to construct the components of the laser device described above, the materials and methods of fabrication will not be described in further detail.

First Exemplary Dental Procedure

A dentist may use a device similar to the laser device 20 described above having a center wavelength in a wavelength range of 2750 nm to 11,600 nm to perform a first exemplary dental procedure. The dentist uses the device (e.g., laser device 20) to produce analgesia to desensitize a portion of the client's mouth (i.e., target tissue) before removing oral tissue from the preconditioned target tissue in the client's mouth while the target tissue is desensitized. This first exemplary dental procedure may be used to treat dental caries such as preparing cavities of different classes of dental decay. The procedure is performed on dental caries in a client's mouth without anesthetic or anesthesia. Once the lesion is desensitized, the same laser device may be used to remove oral tissue from the desensitized area. It is envisioned that the desensitized target tissue may include a client's tooth, gingiva, frenula, or other oral lesions, and the oral tissue removed from the preconditioned area may include enamel, dentin, dental caries such as preparing cavities of different classes of dental decay, gingiva, frenula, or other oral lesions of treatment. In some examples, the laser unit produces light having a center wavelength of 2780 nm, 2960 nm, or 9600 nm. Further, the handpiece has a fiber tip through which light is transmitted. In some examples, the fiber tip has a diameter in a range of 400 μm to 1200 μm. In other examples, the fiber tip has a diameter of 500 μm or 800 μm. The handpiece also includes a nozzle through which distilled water and filtered air may be dispensed as a spray for cooling the target tissue in the client's mouth while light emitted by the operational end of the handpiece is directed toward the target tissue in the client's mouth. The laser device also includes a flow control for varying a rate at which water and air are dispensed from the nozzle.

It is envisioned that a similar dental procedure may be used on an abfraction in a client's mouth without anesthetic or anesthesia. It is also envisioned that the desensitized target tissue may include a client's tooth, gingiva, frenula, or other oral lesions, and the oral tissue removed from the preconditioned area may include enamel, dentin, dental caries, gingiva, frenula, or other oral lesions of treatment.

Prior to use, the dentist adjusts the laser unit to have an optical output power of 0.25 W, to operate in a free running pulsed mode providing 60 μm bursts at a frequency of at least 50 Hz. The dentist also adjusts the flow control to dispense a spray from the nozzle having initial rates of 1% water and 1% air. While the flow control dispenses water and air at the initial rates, the dentist directs light emitted from the operational end of the handpiece toward the cervical lesion defocusing the directed light one mm from the center of the cervical lesion for a first period having a duration of 30 seconds. After the first 30 second period, the dentist adjusts the laser unit to operate in free running pulsed mode at a frequency of 20 Hz while maintaining the other operating parameters and continuing to direct light emitted from the operational end of the handpiece toward the cervical lesion defocusing the directed light one mm from the center of the cervical lesion. Changing the frequency from 50 Hz to 20 Hz increases the energy delivered to the target tissue to continue the desensitizing process. After a second period having a duration of thirty seconds, the dentist decreases the rate at which water and air are dispensed from the nozzle to 0% water and 0% air while maintaining the other operating parameters and defocuses the directed light to five mm to eight mm from the center of the cervical lesion. After a third period having a duration of twenty seconds, the dentist removes the handpiece, so laser light is not directed toward the client's mouth. The laser desensitizing treatment has been found to be effective for two years or longer compared to chemical desensitizing using a chemical desensitizing agent, which may last only a few months. Once the target tissue in the client's mouth is preconditioned, the dentist adjusts the same laser unit for tissue ablation.

Second Exemplary Dental Procedure

A dentist may use a device similar to the first laser device to precondition a tooth for cavity preparation. The dentist adjusts the laser unit to have an optical output power in a power range of 4.5 W to 6.0 W and to operate in H mode at a frequency of 75 Hz. The dentist selects a fiber tip having a diameter of 500 μm or 800 μm and inserts the tip in the handpiece. The dentist also adjusts the flow control to dispense a spray from the nozzle of 50% water and 70% air. With the laser unit and flow control adjusted, the dentist directs light emitted from the fiber tip of the handpiece toward selected target tissue defocusing the directed light one mm from the center of the target tissue in the decaying lesion of the tooth. While aiming at the selected target, the dentist slightly moves the tip in a semicircular pattern. The preconditioning time for each selected target is 20 seconds. Total preconditioning time depends on the number of selected targets involved in the carious lesion. Once the carious lesion is preconditioned, the dentist adjusts the same laser unit for tissue ablation.

Third Exemplary Dental Procedure

A dentist may use a device similar to the second laser device 120' to perform a third exemplary dental procedure. The laser device includes a diode laser having a handpiece operatively connected to the laser unit. The laser is used to produce analgesia in target tissue before performing ablation using a laser device similar to the first laser device 20.

In the third exemplary procedure, the laser unit is a diode laser that produces light having a center wavelength of 800 nm, 810 nm, 815 nm, 940 nm, 980 nm, or 1040 nm. The diode laser produces light having of an energy fluence in an energy fluence range of 50 J/cm$^2$ to 100 J/cm$^2$ in a continuous wave mode.

The handpiece has an operational end from which light is emitted. Preferably, the handpiece is configured to maintain a predetermined target distance between the operational end of the handpiece and the target tissue in the client's mouth when light is directed toward the target tissue in the client's mouth. For example, a handpiece similar to handpiece 180' having a distance guide 190 may be used. Further, the distance guide 190 may be configured such that the handpiece projects a spot of light in the client's mouth having an area of one cm$^2$ when the operational end of the handpiece and the target tissue in the client's mouth are separated by the predetermined target distance.

Prior to administering low level laser therapy to the client's mouth, the dentist adjusts the laser unit to deliver light through the light guide of the handpiece at a selected combination of average optical output power and preconditioning time. For example, the dentist may adjust the diode laser to emit light from the handpiece having an average optical output power in a power range of 1.0 W to 2.5 W in a continuous wave mode. When the output power is 1.0 W in continuous wave mode, it takes 100 seconds to attain 100 J. When the output power is 2.5 W in continuous wave mode, it takes 40 seconds to attain 100 J. After adjusting the laser unit, the dentist uses the handpiece to direct light toward the target tissue in the client's mouth for the selected preconditioning time to produce analgesia in the target tissue in the client's mouth. In this exemplary procedure, the dentist uses a handpiece adapted to maintain a predetermined target distance between the operational end of the handpiece and the target tissue in the client's mouth throughout the selected preconditioning time. As will be appreciated, the laser dosage used is described as low level laser therapy that produces a biostimulation effect or a photobiomodulation effect on the target tissue. It is envisioned that the analgesia procedure of this third exemplary procedure may be performed on a tooth such as a tooth having an amalgam restoration, a tooth having a very deep cavity including a deep cavity in a deciduous or permanent tooth or a deep cavity exposing the pulp. Or the analgesia procedure may be performed at an oral surgery site such as gingiva, a labial frenum in the maxilla or mandible, or gingival hyperplastic tissues in large dental decays.

Once the target tissue in the client's mouth is preconditioned, the dentist may remove oral tissue from the desensitized target tissue using a second laser device similar to the laser device 20 including a laser unit that produces light having a center wavelength of 2780 nm, 2960 nm, or 9600 nm. It is envisioned that the tissue removal procedure may be used for cavity preparation, to remove amalgam using a rotary high speed drill for the purpose of sectioning and removing the amalgam in pieces, to perform a pulpotomy in the deciduous or permanent tooth, to perform a root canal therapy on a tooth that has relatively straight canals, or to perform a gingivectomy or a labial frenectomy of the maxilla or mandible.

Study

A clinical study was performed to verify the efficacy of devices and dental procedures similar to those described in producing analgesia to desensitize a target tissue in a participant's mouth. The study was conducted on a group of adults having at least two cavities of the same general type and size. Two different cavity preparations were performed on each participant. One cavity was preconditioned using low level laser therapy to produce analgesia in the pulp before using higher power to remove material for cavity preparation. The other cavity was prepared without low level laser therapy preconditioning, using only higher power to remove material for cavity preparation. The study participants did not receive anesthesia or anesthetic.

The low level laser therapy was performed using an Er,Cr:YSGG (2780 nm, middle infrared) laser as a laser. The same laser was used to remove material from the preconditioned target tissue to prepare a cavity or perform other dental procedures. This laser was a WATERLASE IPLUS all-tissue laser available from BIOLASE, Inc. of Foothill Ranch, California. Conventional WATERLASE laser consumables including a contra-angle handpiece were used with the laser.

When preconditioning, the laser was set to 0.25 W, 50 Hz, 0% water, 0% air, and H mode. Using a fiber tip having a diameter of 500 μm, the dentist oriented the fiberoptic tip of the handpiece perpendicular to the surface of cervical target tissue in tooth and maintaining a distance of about 2 mm between the fiber tip and the surface being treated. The dentist translated the fiberoptic tip back and forth along an imaginary line having a length of 2 mm while maintaining the 2 mm distance between the tip and the surface being treated for a selected period of time. Material removal was also performed using the same laser. The settings during cavity preparation differed depending upon the particular lesion. For Class I preparations, the laser was set to 4.5 W, 15 Hz, 60% water, and 60% air. Cavity preparation continued using a conventional laser preparation technique. For Class V preparations, the laser was set to 2.0 W, 15 Hz, 60% water, and 60% air and a conventional laser preparation technique was performed to prepare the cavity.

If during the cavity preparation, the participant indicated any pain, the procedure was paused, and the participant was asked to score the pain on a conventional visual analog scale (VAS). The participant was offered anesthetic and when anesthetic was refused cavity preparation resumed using the same settings. VAS is a widely used tool for quantifying pain. The participant is asked to indicate the level of perceived pain along a 100 mm long horizontal line with the left end indicating no pain. The distance from the left end of the line that the participant marks is representative of a level of pain perceived. Up to three VAS measurements were recorded during each cavity preparation. If a participant felt any pain at all during the procedure, they were instructed to raise their hand and the treatment would be paused while the participant recorded their level of pain on the VAS form. After the cavity was prepared, the participant recorded a final level of pain on the VAS form. Participants who did not indicate sensitivity were given a VAS score of zero.

On average, treatments on small lesions had a VAS score of 0.068 for cavities prepared after laser preconditioning and 7.31 for cavities prepared without preconditioning. The lower the VAS score, the lower the perceived pain. All participants were able to tolerate complete cavity preparation regardless of whether laser preconditioning was performed, and all VAS scores fell within the left-most 40 mm of the scale. On average, treatments on medium and large lesions had a VAS score of 4.39 for cavities prepared using laser preconditioning and 16.06 for cavities prepared without preconditioning. All participants were able to tolerate complete cavity preparation regardless of whether laser preconditioning was performed, and all VAS scores fell within the left-most 75 mm of the scale.

In addition, participants were instructed to raise their hand if they felt any pain during treatment. The number of times a participant raised their hand was also used to assess which technique was more comfortable. The fewer times the participant raised a hand, the more comfortable the technique. For small lesions, the total number of hand raises was zero regardless of whether precondition was performed. In the medium or large lesion category, the total number of hand raises without preconditioning was two but with preconditioning the total number of hand raises was zero. The average number of hand raises per participant was 0±0.2115 without preconditioning and zero with laser preconditioning.

The study showed that cavity preparation was substantially painless when laser preconditioning was used on small, medium, and large lesions. Laser preconditioning reduced the level of perceived pain during cavity preparation for medium and large lesions.

Although the devices and procedures are described with reference to dentistry, it is envisioned they are also applicable to the medical and veterinary arts.

When introducing elements in this description, the articles "a", "an", "the", and "said" are intended to mean that there are one or more of the elements. The terms "comprising", "including", and "having" are intended to be inclusive and mean that there may be additional elements other than the listed elements.

As those skilled in the art could make various changes to the above constructions, products, and methods without departing from the intended scope of the description, all matter in the above description and accompanying drawings should be interpreted as illustrative and not in a limiting sense.

The invention claimed is:

1. A laser device for use when removing tissue from a living animal, said device comprising:

- a housing;
- a first laser unit mounted in the housing, said first laser unit being configured to produce light having a center wavelength in a wavelength range of 750 nm to 1400 nm;
- a control unit operatively connected to said first laser unit capable of controlling said first laser unit to emit light having an average optical output power in a power range of 1.0 W to 2.5 W in a continuous wave mode;
- a handpiece operatively connected to said first laser unit for administering a low level laser therapy dose having said energy fluence, the handpiece including an operational end through which light produced by said first laser unit is emitted when administering the low level laser therapy dose to the tissue, said handpiece being adaptable to maintain a target distance between the operational end and the tissue selected to ensure light emitted through the operational end is projected onto an area on the animal of one square centimeter;
- a second laser unit constructed to produce light having a center wavelength in a wavelength range of 2750 nm to 11500 nm, to provide an energy fluence in an energy fluence range of 50 J/cm$^2$ to 100 J/cm$^2$, and to operate in a free running pulsed mode providing 60 μm bursts at a frequency of at least 50 Hz; and
- a light guide operatively connected to said second laser unit adapted to deliver light to the target tissue.

2. A laser device as set forth in claim 1, wherein said first laser unit comprises a diode laser constructed to produce light having a center wavelength selected from a group of wavelengths consisting of 800 nm, 810 nm, 815 nm, 940 nm, 980 nm, and 1040 nm.

3. A laser device as set forth in claim 1, wherein the control unit is capable of controlling said laser unit to emit light having a free running pulse frequency in a frequency range of 10 Hz to 15 Hz.

4. A laser device as set forth in claim 1, wherein the control unit is capable of controlling said laser unit to emit light having a free running pulse frequency in a frequency range of 30 Hz to 50 Hz.

5. A laser device as set forth in claim 1, wherein said second laser unit comprises at least one laser selected from a group of lasers consisting of an Er:YAG solid-state laser, an Er,Cr:YSGG solid-state laser, and a $CO_2$ gas laser.

6. A laser device as set forth in claim 1, wherein:

said handpiece is a first handpiece; and the laser device further comprises:

a second handpiece including a fiber tip having a diameter in a size range of 500 μm to 800 μm through which light is emitted and a nozzle from which a spray is dispensed to cool the target tissue while light emitted from the fiber tip of the second handpiece is directed toward the target tissue; and a flow control operatively connected to the nozzle for varying a rate at which the spray is dispensed from the nozzle, the flow control being configured to vary a water flow rate of water dispensed from the nozzle and to vary an air flow rate of air dispensed from the nozzle; and wherein said second laser unit is adapted to emit light having an average optical output power in a power range of 1.75 W to 2.25 W.

7. A laser device as set forth in claim 1, wherein said second laser is adjustable to produce light having a free running pulse frequency in a frequency range of 10 Hz to 20 Hz.

8. A laser device as set forth in claim 1, wherein said second laser is adjustable to produce light having a free running pulse frequency in a frequency range of 30 Hz to 50 Hz.

9. A laser device for desensitizing target tissue in a client's mouth, said laser device comprising:

a laser unit comprising at least one laser selected from a group of lasers consisting of an Er:YAG solid-state laser, an Er,Cr:YSGG solid-state laser, and a $CO_2$ gas laser;

a handpiece operatively connected to the laser unit including a fiber tip having a diameter in a size range of 500 μm to 800 μm from which light produced by the laser unit is emitted and a nozzle from which a spray comprising water and air is dispensed for cooling the target tissue in the client's mouth while light emitted by the fiber tip of the handpiece is directed toward the target tissue in the client's mouth;

a flow control for varying a rate at which water is dispensed from the nozzle and a rate at which air is dispensed from the nozzle, the flow control being adjustable to dispense water from the nozzle up to a maximum water flow rate and to dispense air from the nozzle up to a maximum air flow rate and to a first water flow rate that is 1% of the maximum water flow rate and to a first air flow rate that is 1% of the maximum air flow rate; and a control unit configured to adjust the laser unit to have an average optical output power of 0.25 W and to operate in a free running pulsed mode providing 60 μm bursts at a frequency of at least 50 Hz and to defocus light directed toward the target tissue by one mm.

10. A laser device as set forth in claim 9, wherein the control unit is configured to adjust the laser unit to have an average optical output power of 0.25 W and to operate in the free running pulsed mode providing 60 μm bursts at a frequency of 20 Hz and to defocus light directed toward the target tissue by one mm.

11. A laser device as set forth in claim 9, wherein:

the flow control is adjustable to prevent air flow through the nozzle and to prevent water flow through the nozzle; and the control unit is configured to adjust the laser unit to defocus light directed toward the target tissue by 5 mm to 8 mm.

12. A laser device for use when ablating soft tissue in a client's mouth, said laser device comprising:

a housing;

a laser unit mounted in the housing, said laser unit being configured to produce light having a center wavelength in a wavelength range of 2750 nm to 11500 nm;

a handpiece operative connected to the laser unit including a fiber tip having a diameter in a size range of 400 μm to 1200 μm through which light is transmitted and a nozzle from which a spray comprising water and air is dispensed to cool the soft tissue in the client's mouth while light emitted from the fiber tip of the handpiece is directed toward the soft tissue in the client's mouth; and a flow control for varying a rate at which the spray is dispensed from the nozzle, said flow control being adjustable to dispense water from the nozzle up to a maximum water flow rate and to dispense air from the nozzle up to a maximum air flow rate and being adjustable to dispense water from the nozzle at a water flow rate in a water flow rate range of 10% to 20% of the maximum water flow rate and to dispense air from the nozzle at an initial air flow rate of 20% of the maximum air flow rate; and a control unit operatively connected to the laser unit configured to adjust the laser unit to have an average optical output power in a power range of 1.75 W to 2.25 W and to operate in a free running pulsed mode providing 60 μm bursts at a frequency of at least 50 Hz.

* * * * *